(12) United States Patent
Tanabe et al.

(10) Patent No.: US 10,286,185 B2
(45) Date of Patent: May 14, 2019

(54) CATHETER ASSEMBLY

(71) Applicant: Terumo Kabushiki Kaisha, Tokyo (JP)

(72) Inventors: Hidenori Tanabe, Tokyo (JP); Takao Anzai, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1034 days.

(21) Appl. No.: 14/033,717

(22) Filed: Sep. 23, 2013

(65) Prior Publication Data

US 2014/0074034 A1 Mar. 13, 2014

Related U.S. Application Data

(63) Continuation of application No. PCT/JP2012/057964, filed on Mar. 27, 2012.

(30) Foreign Application Priority Data

Mar. 28, 2011 (JP) .................................. 2011-069806

(51) Int. Cl.
*A61M 25/06* (2006.01)
*A61M 39/06* (2006.01)
*A61M 25/00* (2006.01)

(52) U.S. Cl.
CPC .... *A61M 25/0606* (2013.01); *A61M 25/0097* (2013.01); *A61M 39/0693* (2013.01); *A61M 2039/0633* (2013.01)

(58) Field of Classification Search
CPC ...... A61M 2039/0633; A61M 35/0606; A61M 25/0606; A61M 25/0097; A61M 39/0693

(Continued)

(56) References Cited

U.S. PATENT DOCUMENTS 4,774,963 A * 10/1988 Ichikawa et al. ............. 600/576
5,242,411 A * 9/1993 Yamamoto et al. ..... 604/167.04

(Continued)

FOREIGN PATENT DOCUMENTS

JP 2000-279527 A 10/2000
JP 2002-263197 A 9/2002

(Continued)

OTHER PUBLICATIONS

International Search Report issued in Application No. PCT/JP2012/057964 dated Jul. 3, 2012.

*Primary Examiner* — Nathan R Price
*Assistant Examiner* — Anh Bui
(74) *Attorney, Agent, or Firm* — Foley & Lardner LLP (57) ABSTRACT

A catheter assembly includes a hollow catheter; a catheter hub fixed onto a base end portion of the catheter, the catheter hub having an internal passage communicating with an inside of the catheter; a needle disposed in the catheter; a needle hub; a valve element including an opening and closing unit configured to be opened and closed; an operation member including a tubular body, the operation member being configured such that an opening portion of the operation member is insertable into the opening and closing unit to cause the base end side and a tip side of the catheter hub to communicate with each other; a communication unit; and a sealing member including a tubular body, the sealing member being disposed at a base end side of the valve element and being configured to allow the passage of air and prohibit the passage of liquid.

9 Claims, 7 Drawing Sheets (58) Field of Classification Search
USPC ............ 604/167.03, 167.04, 167.06, 164.08
See application file for complete search history.

(56) References Cited

U.S. PATENT DOCUMENTS

| | | | |
|---|---|---|---|
| 5,980,492 A * | 11/1999 | Rosen et al. ............. | 604/168.01 |
| 2005/0043684 A1* | 2/2005 | Basta et al. .............. | 604/164.13 |
| 2007/0196414 A1* | 8/2007 | Hammarsten et al. ....... | 424/422 |
| 2010/0204648 A1* | 8/2010 | Stout et al. .................. | 604/122 |

FOREIGN PATENT DOCUMENTS

| | | |
|---|---|---|
| JP | 2003-135602 A | 5/2003 |
| JP | 2005-237639 A | 9/2005 |
| JP | 2005-349196 A | 12/2005 |
| JP | 2010-088521 A | 4/2010 |

* cited by examiner

CATHETER ASSEMBLY

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2012/057964 filed on Mar. 27, 2012, which is based upon and claims the benefit of priority of Japanese Application No. 2011-069806 filed on Mar. 28, 2011, the entire contents of which are hereby incorporated by reference in their entireties.

BACKGROUND

The present disclosure relates to a catheter assembly.

A patient receives a transfusion by puncturing a blood vessel of the patient with a catheter assembly connected to a transfusion line and indwelling the catheter assembly in the blood vessel.

The catheter assembly is configured to include a hollow catheter, a catheter hub fixed onto a base end of the catheter, a needle which is inserted into the catheter and has a sharp needle point at the tip, and a needle hub fixed onto a base end of the needle (for example, see Japanese Patent Publication No. JP-A-2002-263197). In addition, a valve element (hemostasis valve) and an operation member (pusher) performing opening and closing operations of the valve element are accommodated in the catheter hub.

The valve element accommodated in the catheter hub has a function of preventing leakage of blood flowing into a passage of the catheter hub via the catheter securing a blood vessel. Particularly, the catheter assembly of Japanese Patent Publication No. JP-A-2002-263197 has a groove portion in which the valve element is formed on an outer peripheral surface thereof such that air confined between blood, flowing into the passage, and the valve element can be released via the groove portion. Accordingly, air bubbles are prevented from remaining in the passage such that the inflow of blood reliably takes place.

In the valve element of the catheter assembly or the catheter assembly of Japanese Patent Publication No. JP-A-2002-263197, although air confined between blood flowing into a passage and the valve element can be released, it is possible for blood which has flowed into the passage via a groove portion to infiltrate a base end side of the valve element.

Blood infiltrating the base end side of the valve element from the groove portion remains between the valve element and an operation member even after administration of a liquid medicine performed by connecting an infusion set or a syringe thereto is completed, thereby resulting in a possible proliferation source of bacteria or a thrombus formation.

Embodiments of the present invention have been made taking the above-mentioned circumstances into consideration, and an object of embodiments of the invention is to provide a catheter assembly in which it is difficult for blood to infiltrate between the valve element and the operation member when puncturing a blood vessel.

SUMMARY

In one embodiment, a catheter assembly comprises a hollow catheter; a catheter hub fixed onto a base end portion of the catheter, the catheter hub having an internal passage communicating with an inside of the catheter; a needle disposed in the catheter; a needle hub fixed to a base end portion of the needle, the needle hub being connectable to a base end side of the catheter hub; a valve element positioned to block the internal passage of the catheter hub, the valve element including an opening and closing unit configured to be opened and closed; an operation member including a tubular body, the operation member being configured such that an opening portion of the operation member is insertable into the opening and closing unit to cause the base end side and a tip side of the catheter hub to communicate with each other; a communication unit disposed on at least one of (i) an inner periphery portion of the catheter hub where the valve element is positioned, and (ii) a peripheral edge portion of the valve element, the communication unit being configured to allow the base end side and the tip side of the catheter hub to communicate with each other; and a sealing member including a tubular body, the sealing member being disposed at a base end side of the valve element and being configured to allow the passage of air and prohibit the passage of liquid.

DETAILED DESCRIPTION

According to embodiments of the present invention, there is provided a catheter assembly including: a hollow catheter; a catheter hub, fixed onto a base end portion of the catheter, internally having a passage communicating with the inside of the catheter; a needle inserted into the catheter; a needle hub, fixed onto a base end portion of the needle, capable of being connected to a base end side of the catheter hub; a valve element, positioned to block the passage, having an opening and closing unit capable of being opened and closed; an operation member having a tubular body, provided such that one opening portion thereof is inserted into the opening and closing unit to cause the base end side and a tip side of the catheter hub to communicate with each other; and a communication unit, provided on an inner periphery portion of the catheter hub provided with the valve element or a periphery edge portion of the valve element, causing the base end side and the tip side of the catheter hub to communicate with each other. In the catheter assembly, a sealing member (liquid impermeable) has a tubular body, and is provided between the valve element and the operation member so as to block the communication unit, allowing the passage of air yet prohibiting the passage of liquid.

Since the catheter assembly according to the invention is provided with the sealing member between the valve element and the operation member, even in a case where liquid such as blood flows over the valve element and reaches the base end side, it is possible to inhibit the liquid from infiltrating between the sealing member and the operation member, that is, the base end side of the sealing member provided in to tightly contact the valve element.

In one embodiment of the invention, it is preferable that the sealing member be a porous body.

The porous body can allow the passage of air yet does not allow the passage of liquid. Accordingly, if the aforementioned sealing member is employed, even in a case where liquid such as blood reaches the base end side of the valve element, it is possible to prohibit blood from infiltrating between the sealing member and the operation member.

In one embodiments of the invention, it is preferable that the sealing member have a tubular molded article, include at least one of a hole portion passing through from one end surface, in which the molded article tightly contacts the valve element to the other end surface, and an outer periphery groove portion formed on the outer periphery surface, and the other end surface be provided with a hydrophobic filter. In addition, it is preferable that at least one portion of the hole portion and the outer periphery groove portion be coated with a water-swelling polymer.

The hydrophobic filter allows the passage of air yet blocks the passage of liquid. Accordingly, if the hydrophobic filter is provided on the other end surface of the sealing member, even in a case where liquid such as blood reaches the base end side of the valve element through at least one of the hole portion and the outer periphery groove portion, it is possible to prevent blood from infiltrating the base end side flowing over the hydrophobic filter provided in the sealing member.

In addition, as described below, since the water-swelling polymer absorbs liquid such as water or blood so as to swell, it is possible to more reliably prevent blood from infiltrating the base end side flowing over the hydrophobic filter provided in the sealing member.

In one embodiment of invention, it is preferable that the sealing member have the tubular molded article, and include at least one of a hole portion passing through from one end surface in which the molded article tightly contacts the valve element to the other end surface and an outer periphery groove portion formed on the outer periphery surface, and at least one portion of the inside of the hole portion and the inside of the outer periphery groove portion be coated with a water-swelling polymer.

The water-swelling polymer absorbs liquid such as water or blood so as to swell. Accordingly, if at least one portion of the hole portion and the outer periphery groove portion formed on the sealing member is coated with the water-swelling polymer, it is possible to allow the passage of air through the hole portion or the outer periphery groove portion. Then, in a case where liquid such as blood infiltrates the base end side flowing over the valve element, the water-swelling polymer swells by contacting the liquid, thereby blocking the hole portion or the outer periphery groove portion. Accordingly, it is possible to inhibit liquid such as blood from infiltrating between the sealing member and the operation member.

According to an embodiment of the invention, it is possible to provide a catheter assembly in which it is difficult for blood to infiltrate between a sealing member, provided to tightly contact a valve element, and an operation member.

Hereinafter, a catheter assembly according to an embodiment of the invention will be described in detail referring to the appropriate views. Moreover, hereinafter, for convenience of description, the right side in FIGS. 1 to 4 denotes a "base end", and the left side therein denotes a "tip". Further, the "tip" denotes a blood vessel puncturing side.

Figure 1:
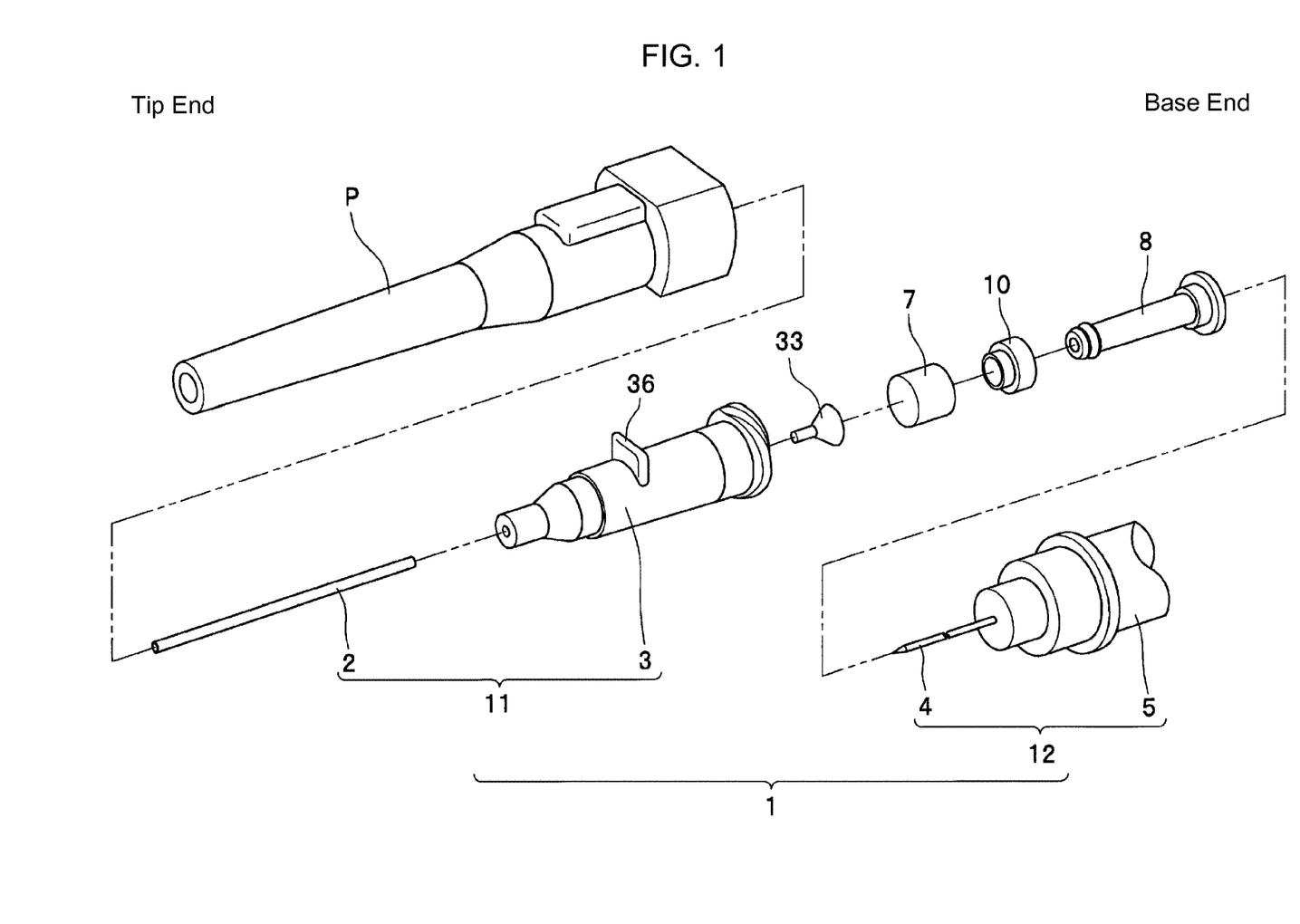
FIG. 1 is an exploded perspective view of a catheter assembly according to one embodiment.

As illustrated in FIG. 1, a catheter assembly 1 according to the embodiment is configured to have an indwelling catheter 11 and a puncturing needle 12. A protector P is attached to the catheter assembly 1 for protecting the indwelling catheter 11.

The catheter assembly 1 having the above-mentioned configuration obtains an assembled state (state illustrated in FIGS. 1 and 2) where the indwelling catheter 11 and the puncturing needle 12 are assembled, and an evulsed state (state illustrated in FIG. 3) where the puncturing needle 12 is evulsed from the indwelling catheter 11. The catheter assembly 1 can be used for puncturing a surface of a living body in the assembled state. Thereafter, the indwelling catheter 11 can be indwelled in the surface of a living body by switching into the evulsed state. It is possible to connect a connector 20 to the indwelling catheter 11 indwelled in the surface of a living body (see FIG. 4).

Here, before describing the catheter assembly 1, the connector 20 will be described referring to FIG. 4.

Figure 4:
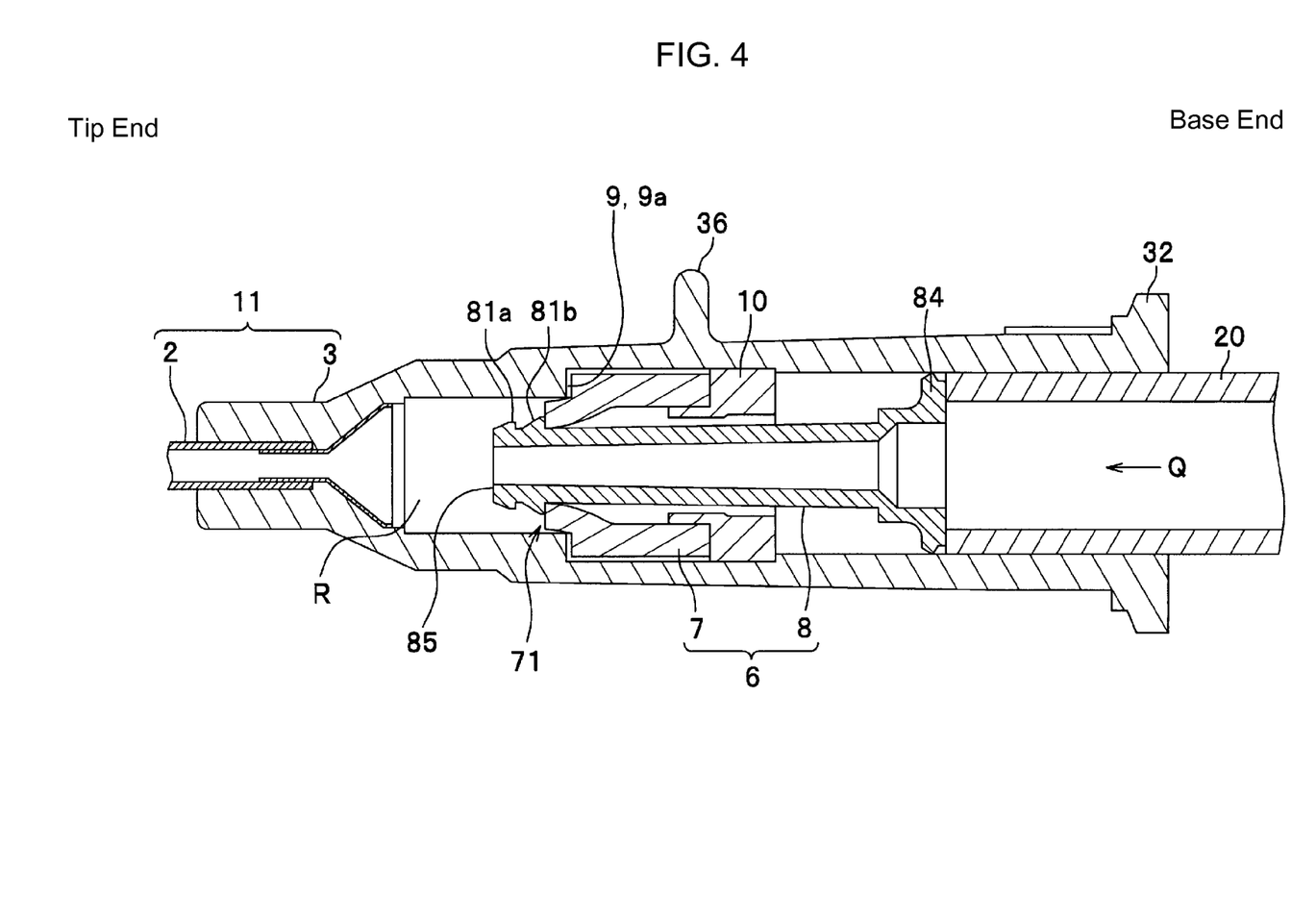
FIG. 4 is a longitudinal sectional view of the catheter assembly to which a connector is connected according to one embodiment.

As illustrated in FIG. 4, the connector 20 has a tubular body and is connected to a base end portion of the indwelling catheter 11. A tip portion of a tube (not illustrated) is connected to the base end portion of the connector 20. Then, a bag (not illustrated) filled with an infusion solution Q is connected to a base end portion of the tube. The infusion solution Q is supplied from the bag in a connected state where the connector 20 is connected to the indwelling catheter 11 (see FIG. 4).

Further, in order to reliably supply the infusion solution Q, it is preferable that the connector 20 have a locking mechanism (not illustrated) which is engaged with a locking unit 32 provided on an outer periphery of the base end portion of the indwelling catheter 11 to be fixed.

In addition, a tip portion of the connector 20 connected to the base end portion of the indwelling catheter 11 may have a tapered shape in which the outer diameter thereof is gradually decreased toward the tip. Accordingly, when connecting the connector 20, it is possible to easily insert the connector 20 into the base end portion of the indwelling catheter 11. In addition, after the infusion solution Q is supplied, the connector 20 can be easily removed from the base end portion of the indwelling catheter 11. That is, it is possible to easily perform insertion and evulsion operations of the connector 20 with respect to the indwelling catheter 11.

Returning to FIG. 1, the description of the catheter assembly 1 according to the embodiment will be continued.

The indwelling catheter 11 is configured to mainly include a hollow catheter 2 and a catheter hub 3, fixed onto a base end portion of the catheter 2, internally having a passage 31 which communicates with the inside of the catheter 2. In addition, in order to facilitate a manual approaching technique with the catheter 2 toward a blood vessel, it is preferable that the catheter hub 3 have a tab 36 protruding from an outer periphery surface.

It is preferable that the catheter 2 be a tube that is flexible to some extent. A resin material, and particularly, a soft resin material, is suitable for the catheter 2 as a component material. Specifically, for example, a fluorine-based resin such as polytetrafluoroethylene (PTFE), ethylene-tetrafluoroethylene copolymer (ETFE) and perfluoroalkoxy fluorine resin (PFA); olefin-based resin such as polyethylene and polypropylene or a mixture thereof; polyurethane; polyester; polyamide; polyether nylon resin; or a mixture of the olefin-based resin and ethylene-vinyl acetate copolymer may be used.

It is preferable that the inside of the catheter 2 have visibility to be visually perceivable in its entirety or in a part. That is, it is preferable that the catheter 2 be constituted by a resin which is transparent (colorless transparent), colored transparent or semi-transparent. Accordingly, when the catheter 2 secures a blood vessel, it is possible to visually check a phenomenon (flashback) in which blood R (see FIG. 4) flows into the transparent catheter hub 3 through an intracavity 21 of the catheter 2.

In addition, it is also possible to mix an X-ray contrast agent such as barium sulfate, barium carbonate, bismuth carbonate or tungstic acid for the component material of the catheter 2 to impart a contrast imaging function.

Figure 2:
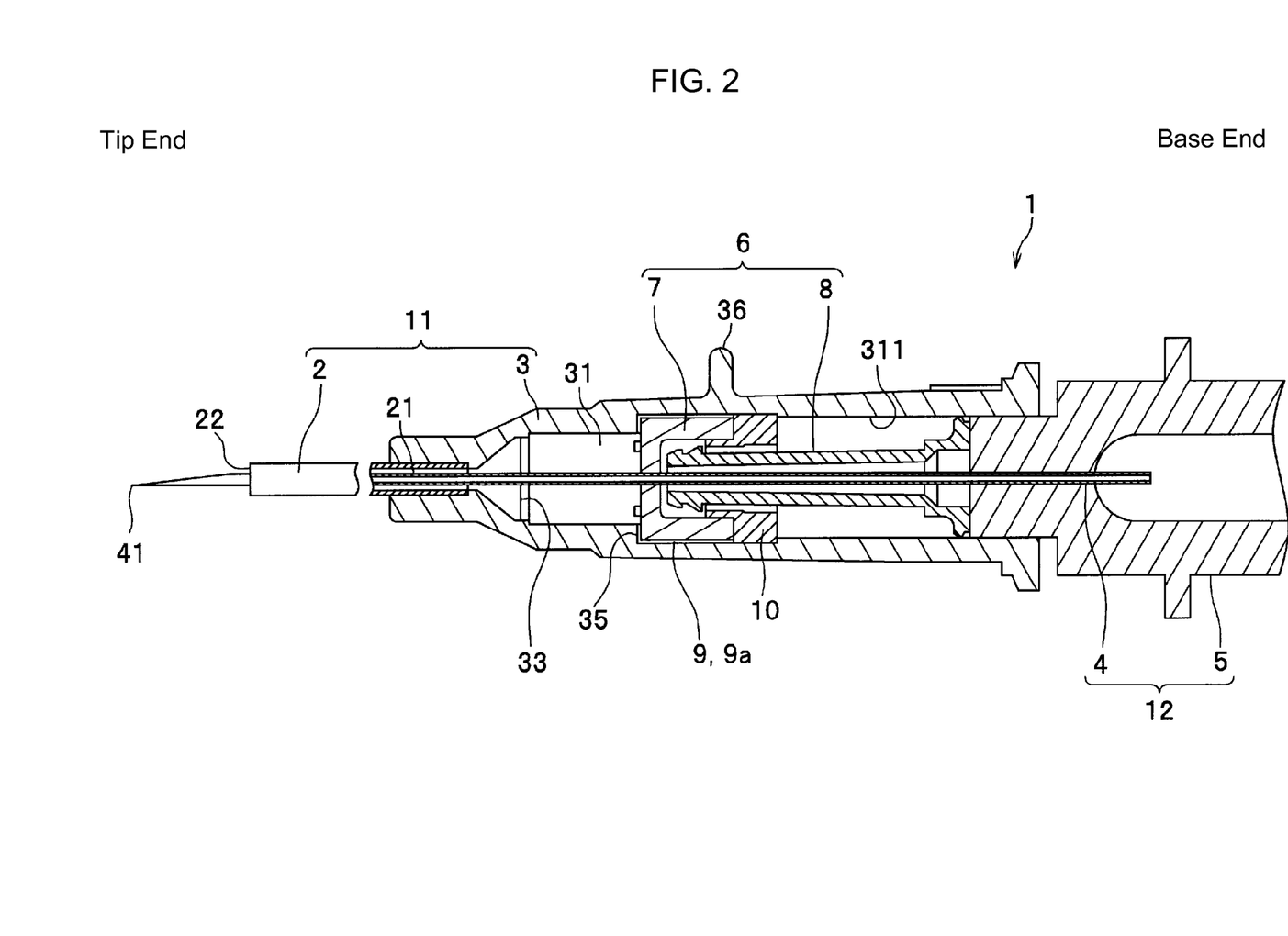
FIG. 2 is a longitudinal sectional view of the catheter assembly according to one embodiment.
Figure 3:
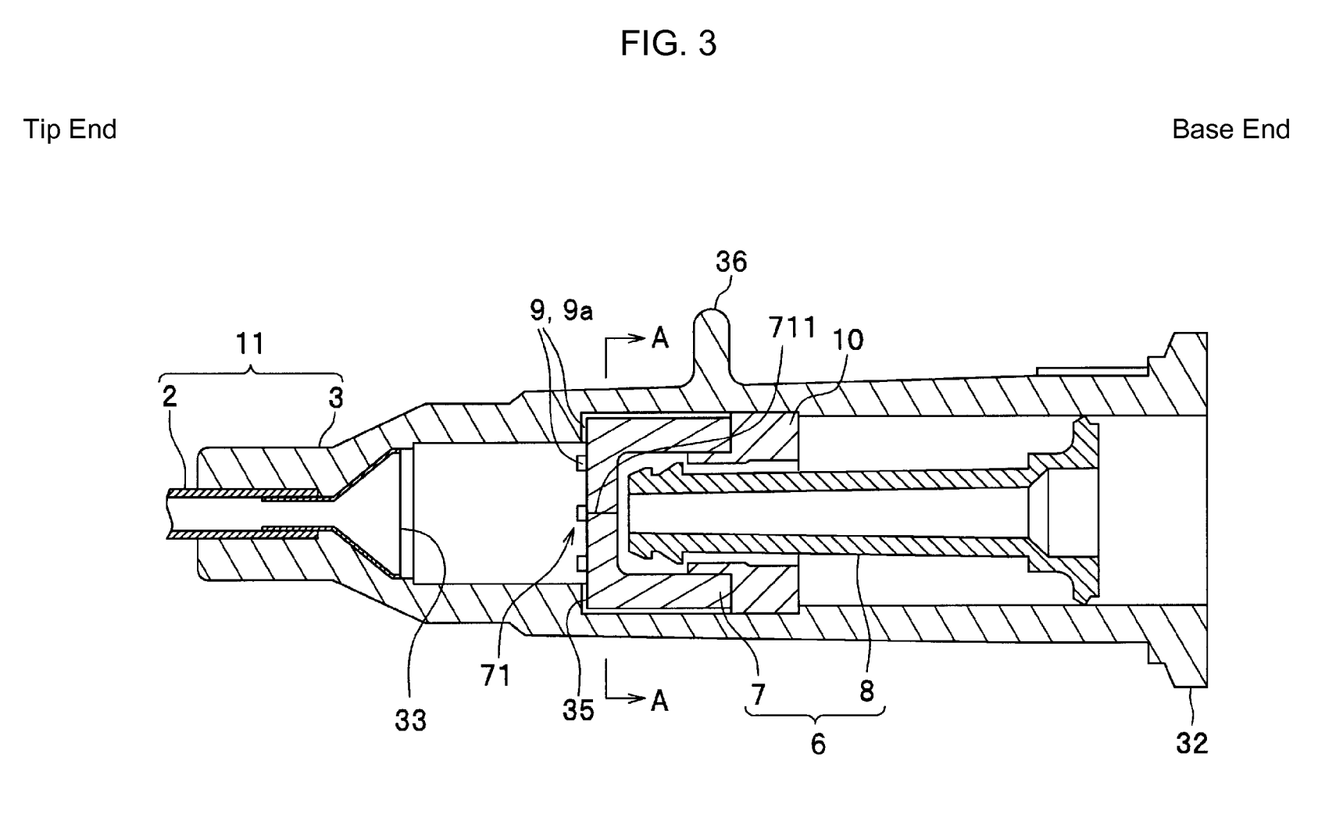
FIG. 3 is a longitudinal sectional view of the catheter assembly according to one embodiment, in which a puncturing needle is evulsed.

For example, the base end portion of the catheter 2 is liquid-tightly fixed onto the catheter hub 3 by caulking, fusing (heat fusing, high-frequency fusing or the like) or bonding using a bonding agent. Further, FIGS. 2 and 3 illustrate a state where the catheter 2 and the catheter hub 3 are fixed to each other by a caulking pin 33. The caulking pin 33 has a circular tube portion at the tip side and a tapered portion gradually increased in diameter from the circular tube portion toward the base end side. In other words, the caulking pin 33 is gradually decreased in diameter from the base end side toward the tip side. Therefore, if the infusion solution Q flows in from the base end side, it is possible to cause the infusion solution Q to smoothly flow out toward the catheter 2. Since the catheter 2 and the catheter hub 3 are caulked at the circular tube portion, it is preferable that the caulking pin 33 be made of metal or hard resin. In a case where the catheter 2 and the catheter hub 3 are fixed to each other by the fusing or the bonding agent, it is possible not to employ the caulking pin 33 (not illustrated). In addition, in this case, in place of the above-described tapered portion, the inner diameter of the passage 31 of the tip portion is to set for the tapered portion gradually decreased in the tip direction, thereby enabling the infusion solution Q to smoothly flow out toward the catheter 2 when the infusion solution Q flows in from the base end side.

As illustrated in FIG. 2, the catheter hub 3 is constituted by a member having a tubular body such that an intracavity portion thereof functions as the passage 31. The passage 31 communicates with the intracavity 21 of the catheter 2.

It is preferable that the base end portion of the passage 31 of the catheter hub 3 have a tapered shape in which the inner diameter of a wall portion 311 thereof is gradually increased toward the base end direction. It is further preferable that the tapering of the base end portion of the passage 31 of the catheter hub 3 and the tapering of the tip of the connector 20 be formed in mutually corresponding shape (tapering angle). Accordingly, it is possible to easily insert the tip of the tapered connector 20 into the corresponding base end portion of the tapered catheter hub 3 to be connected thereto. In addition, in this connecting manner, the wall portion 311 of the passage 31 tightly contacts the outer periphery portion of the connector 20, thereby maintaining a further liquid-tight state.

In addition, in the middle of the passage 31, it is preferable that a step difference portion 35 having a tip side reduced in diameter with respect to the base end side be formed. If an end surface of the tip side of the valve element 7 to be described below is provided to abut on the step difference portion 35, the valve element 7 can be stably fixed thereto.

In addition, in the embodiment, as illustrated in FIGS. 1 to 4, the valve element 7 is provided so as to block the passage 31. Specifically, as illustrated in FIG. 3, the valve element 7 having a bottomed tubular shape is fixed such that the outer periphery surface of the side wall contacts the inner periphery surface of the catheter hub 3. An opening and closing unit 71 (see FIG. 4) capable of being opened and closed is provided at the bottom portion of the valve element 7. The valve element 7 is a part of a valve mechanism 6 including the opening and closing unit 71, and an operation member 8 to be described below.

The opening and closing unit 71 is configured to include a slit 711 (see FIGS. 3 and 5) passing through in the thickness direction, to be formed at the center part of the bottom portion. The shape of the slit 711 may be formed without any particular limitation as long as the operation member 8 can be inserted into the slit and removed. For example, the bottom portion in a plan view can be formed in a shape of straight line, cross, letter Y ("TO" in KATAKANA of Japanese character). Accordingly, the opening and closing unit 71 not only allows the operation member 8 to be inserted into and removed from, but also becomes reliably self-occlusive.

It is preferable that the valve element 7 be composed of an elastic material having a tightness which is not easily opened by a blood flow. If the valve element 7 is composed of the elastic material, it is possible to smoothly open and close the opening and closing unit 71. As the elastic material composing the valve element 7, for example, various rubber materials such as natural rubber, isoprene rubber, isobutylene-isoprene rubber, butadiene rubber, styrene butadiene rubber, urethane rubber, nitrile rubber, acrylic rubber, fluororubber, and silicone rubber (particularly, vulcanized rubber); various thermoplastic elastomers such as urethane-based, polyester-based, polyamide-based, olefin-based, and styrene-based; or various elastic materials such as mixture of aforementioned materials can be exemplified. Among the elastic materials, particularly, it is preferable that isoprene rubber be employed. If isoprene rubber is employed as the component material of the valve element 7, there are advantages such as a low permanent compression set and a long duration period of the product.

The operation member 8 having a tubular body is provided to have one (at the tip side) opening portion 85 thereof (see FIG. 4) inserted into the opening and closing unit 71 of the valve element 7 so as to cause the base end side and the tip side of the catheter hub 3 to communicate with each other. Accordingly, in the valve mechanism 6, the operation member 8 moves along the axial direction of the passage 31 to cause the one opening portion 85 to be inserted into and removed from the opening and closing unit 71 of the valve element 7, thereby performing shut-off (see FIG. 3) and opening (see FIG. 4) of the passage 31.

Since the valve mechanism 6 illustrated in FIG. 3 has the entire operation member 8 closer to the base end side than the opening and closing unit 71, the opening and closing unit 71 is closed due to the self-occlusive property, thereby shutting off the passage 31. On the other hand, the valve mechanism 6 illustrated in FIG. 4 has the opening portion 85 at the tip side of the operation member 8 positioned at the tip side passing through the opening and closing unit 71. Therefore, the passage 31 is opened via the intracavity location of the operation member 8.

As illustrated in FIG. 4, on the tip outer periphery portion of the operation member 8, there are formed two tip diameter expanded portions 81a and 81b of which the outer diameter is expanded, that is, protruding along the peripheral direction. The tip diameter expanded portion 81b of the tip diameter expanded portions 81a and 81b functions as an engagement portion engaging with the opening and closing unit 71 of the valve element 7 when the operation member 8 passes through the opening and closing unit 71 to cause the passage 31 to be open. The tip diameter expanded portion 81b engages with the opening and closing unit 71 of the valve element 7 to prevent the operation member 8 from accidentally moving toward the base end direction, thereby reliably maintaining the open state of the passage 31.

In addition, it is preferable that the tip diameter expanded portions 81a and 81b be respectively in a tapered shape. Accordingly, when the operation member 8 passes through the opening and closing unit 71 of the valve element 7, the tip diameter expanded portions 81a and 81b are capable of reliably pushing and outwardly widening the opening and closing unit 71 in sequence thereof, thereby easily performing the passing-through. Then, the parts (tip diameter expanded portions 81a and 81b) passing through the opening and closing unit 71 of the operation member 8 are protruding from the opening and closing unit 71.

As described above, the operation member 8 is configured to be in a tubular body. Therefore, when the operation member 8 moves, the outer periphery portion of the operation member 8, for example, a base end diameter expanded portion 84 (see FIG. 4) slides on the wall portion 311 of the passage 31. Accordingly, the movement is stably performed.

It is preferable that the inner diameter of the base end diameter expanded portion 84 be the same or larger than the inner diameter of the connector 20. Accordingly, when the connector 20 is connected to the base end portion of the catheter hub 3, it is possible to easily and reliably cause the infusion solution Q to flow from the connector 20 to the operation member 8.

In the embodiment, a communication unit 9 (see FIGS. 2 to 5) is provided to cause the base end side and the tip side of the catheter hub 3 to communicate with each other. The communication unit 9 is located in the inner periphery portion of the catheter hub 3 where the valve element 7 is provided, or in the periphery edge portion of the valve element 7.

Figure 5:
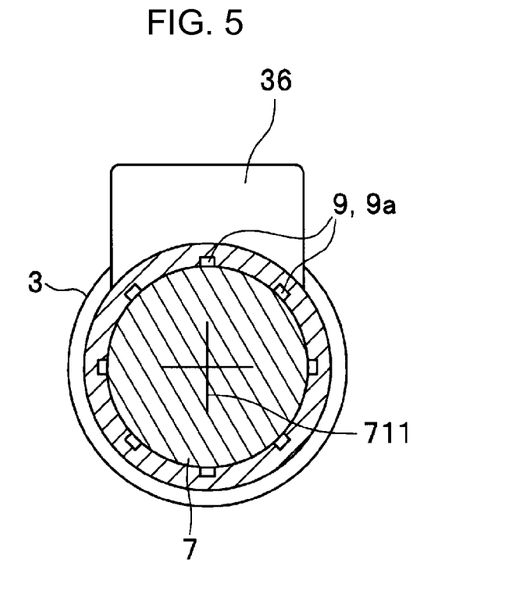
FIG. 5 is a cross-sectional view of an indwelling catheter taken along the line A-A of FIG. 3, and is illustrates a state where eight communication units are provided.

Specifically, as illustrated in FIG. 5, in the middle of the passage 31 of the catheter hub 3, there is formed one or more inner periphery groove portions 9a along the catheter hub 3 in the axial direction from the above-mentioned step difference portion 35 as the communication unit 9.

The inner periphery groove portion 9a is provided to prevent air from remaining inside the catheter hub 3, when the needle 4 is evulsed after puncturing a surface of a living body with the catheter 2 and the needle 4. That is, when the needle 4 is evulsed, air closer to the tip side than the valve element 7 is pushed by the flow of the blood R into the passage 31 to pass through the inner periphery groove portion 9a, thereby being discharged to the base end side. Further, the shape of the inner periphery groove portion 9a is not particularly limited in shape as long as the inner periphery groove portion 9a can exhibit the above-mentioned function. For example, the shape of the inner periphery groove portion 9a may be formed in a linear fashion on the inner periphery surface of the catheter 2 from the tip side to the base end side, in a corrugated fashion, or in a fashion forming a spiral. In addition, the depth of the inner periphery groove portion 9a is not particularly limited as long as the above-mentioned function can be exhibited. For example, the depth thereof can be set to approximately 5 μm to 20 μm.

In an embodiment of the invention, a sealing member 10 is provided at a space between the valve element 7 and the operation member 8, that is, at the base end side of the valve element 7 so as to block the communication unit 9. The sealing member 10 having a tubular body tightly contacts the valve element 7 so as to block the inner periphery groove portion 9a in order to be sealable, while allowing the passage of air yet prohibiting the passage of liquid. It is preferable that the sealing member 10 be faucet-jointed to the valve element 7 to be improved in a tightly contacting state. The sealing member 10 can be fixed onto the inner periphery surface of the catheter hub 3 by fusing or a bonding agent. In the valve element 7, displacement of the base end side is suppressed by the sealing member 10 and displacement of the tip side is suppressed by the step difference portion 35. Accordingly, fluctuations of the position are suppressed regardless of the insertion and removal of the operation member 8, and thus it is possible to smoothly perform the opening and closing operation of the valve element 7.

Further, if the communication unit 9 is provided on the periphery edge portion of the valve element 7, the communication unit 9 may be either a through hole passing through the periphery edge portion of the valve element 7, or an outer periphery groove provided on the outer periphery surface of the valve element 7.

The employed sealing member 10 is to allow the passage of air yet does not allow the passage of liquid. As the sealing member 10, for example, it is possible to properly employ a sealing member formed in a porous body such as a sintered body made of polyethylene. The sealing member 10 having a porous body is easy to manufacture, thereby having an advantage in which the sealing member 10 can be precisely manufactured.

Figure 6A:
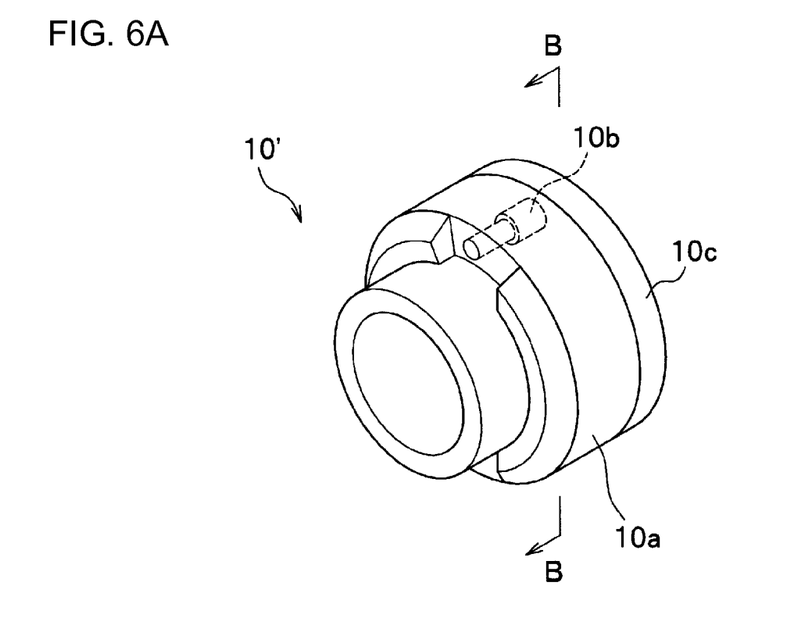
FIGS. 6A and 6B are views illustrating another aspect of a sealing member, FIG. 6A being a perspective view, and FIG. 6B being a cross-sectional view taken along the line B-B of FIG. 6A.
Figure 6B:
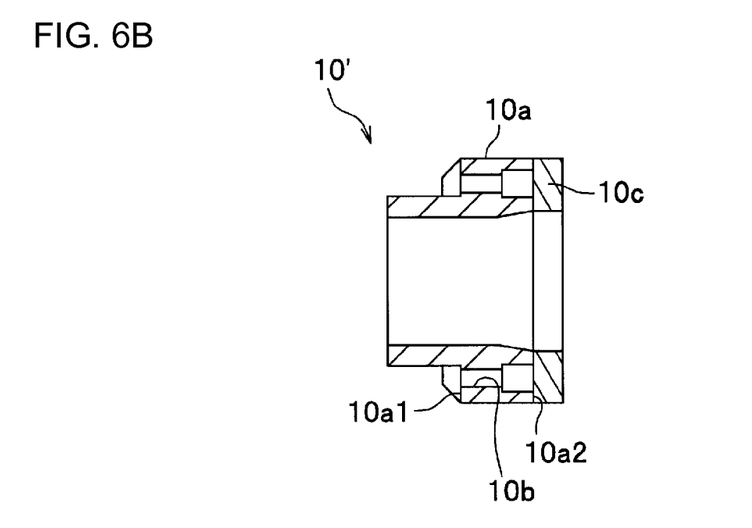

As another example of the sealing member 10, the sealing member 10' illustrated in FIGS. 6A and 6B can be used. In the sealing member 10', there are formed a molded article 10a made of a resin material and molded in a tubular body, and at least one of (i) a hole portion 10b passing through from one end surface 10a1 tightly contacting the valve element 7 of the molded article 10a to the other end surface 10a2, and (ii) an outer periphery groove portion (not illustrated in FIGS. 6A and 6B) formed on the outer periphery surface, while disposing a hydrophobic filter 10c on the other end surface 10a2. It is also possible to coat at least one portion of the hole portion 10b and the outer periphery groove portion of the sealing member 10' with a water-swelling polymer. As the water-swelling polymer to coat with, a water-swelling polymer which is the same as a water-swelling polymer 10e to be described below can be employed.

As the hydrophobic filter 10c, for example, a monolayer sheet or a multilayer sheet made of an olefin resin such as polyethylene or polypropylene, having the thickness of 0.03 mm to 0.3 mm can be employed.

Figure 7:
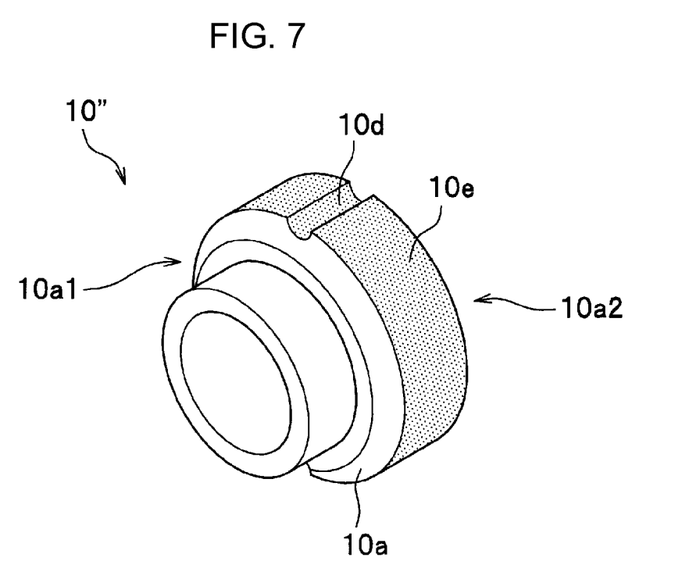
FIG. 7 is a perspective view illustrating still another aspect of the sealing member.

As yet another example of the sealing member 10, a sealing member 10″ illustrated in FIG. 7 can be used. The sealing member 10″ having the molded article 10a made of a resin material and molded in a tubular body, includes at least one of a hole portion (not illustrated in FIG. 7) passing through from one end surface 10a1 in which the molded article 10a tightly contacts the valve element 7 to the other end surface 10a2 and an outer periphery groove portion 10d formed on the outer periphery surface. At least one portion of the inside of the hole portion and the inside of the outer periphery groove portion 10d is coated with the water-swelling polymer 10e.

For example, as the water-swelling polymer 10e: polyvinyl-pyrrolidone; methyl vinyl ether-maleic anhydride copolymer; an acrylamide-acrylate copolymer such as a dimethylacrylamide-glycidyl meta acrylate copolymer; a water-soluble synthetic macromolecule such as sodium polyacrylate, polyacrylamide, polystyrene sulfonate, polyvinyl alcohol, polyethylene oxide and polyethyleneimine; a water-soluble semi-rigid macromolecule such as carboxymethyl starch, dialdehyde starch, carboxymethyl cellulose and hydroxyethyl cellulose; a water-soluble natural macromolecule such as tannin, lignin, alginic acid, gum Arabic, guar gum, gum tragacanth, gelatin, casein and collagen can be used.

For example, as the molded article 10a, various resin materials such as: polyethylene, polypropylene, polyolefin such as ethylene-vinyl acetate copolymer, polyurethane, polyamide, polyester, polycarbonate, polybutadiene, and polyvinyl chloride can be employed.

As illustrated in FIGS. 1 and 2, the puncturing needle 12 is configured to include the needle 4 and a needle hub 5.

As illustrated in FIG. 2, the base end portion of the needle 4 is fixed onto the needle hub 5. When the catheter assembly 1 is in a assembled state, the needle 4 is configured to be inserted into the catheter 2, the valve element 7 and the operation member 8 such that a sharp needle point 41 of the needle 4 protrudes from the tip opening portion 22 of the catheter 2. Then, the needle point 41 is used for the paracentesis into a surface of a living body. In addition, in the aforementioned state, the tip of the needle hub 5 is inserted into the base end portion of the catheter hub 3 to be fitted thereto.

A groove (not illustrated) may be provided at the outer periphery portion of the needle 4 along the axial direction of the needle 4. The groove functions as an introduction passage introducing the blood R into the intracavity 21 of the catheter 2 when the blood vessel is punctured. The blood R introduced from the groove flows into a gap between the needle 4 and the catheter 2. Accordingly, it is possible to reliably check the flashback of the blood R from an early stage. Then, the blood R passes through the intracavity 21 of the catheter 2 to flow into the passage 31 of the catheter hub 3.

For example, as a component material of the needle 4, a metal material such as stainless steel, aluminum or aluminum alloy, titanium or titanium alloy can be used.

The needle hub 5 fixed (adhered) to the base end portion of the needle 4, having a tube shape, includes an air filter (not illustrated) to be disposed at the base end opening portion.

It is preferable that the catheter hub 3, the operation member 8 and the needle hub 5 described above be made of a resin which is transparent (colorless transparent), colored transparent or semi-transparent, thereby securing visibility of the inside thereof. Accordingly, when the catheter 2 secures the blood vessel, the flashback of the blood R can be visually checked.

For example, as the component material of the catheter hub 3, the operation member 8 and the needle hub 5, various resin materials such as polyethylene, polypropylene, polyolefin such as ethylene-vinyl acetate copolymer, polyurethane, polyamide, polyester, polycarbonate, polybutadiene and polyvinyl chloride can be used.

The above-described catheter assembly 1 according to the embodiment is used as follows.

First, a protector P of the catheter assembly 1 in a state where the needle 4 is inserted into the catheter 2 is removed. Next, the catheter hub 3 is grasped to puncture a patient with the needle 4. If the blood vessel is secured by the catheter 2, the blood R flows to the base end direction through the space between the catheter 2 and the needle 4 based on the blood pressure. Since the catheter 2 or the catheter hub 3 is formed of a material which is colorless transparent, colored transparent or semi-transparent, flow of the blood R is visually perceivable. The flow of the blood R reaches a place where the valve element 7 of the passage 31 is positioned. At this time, air confined between the blood R and the valve element 7 is discharged to the base end side of the sealing member 10 (10' and 10") via the sealing member 10 (10' and 10") passing through the communication unit 9 (inner periphery groove portion 9a). After the flow of the blood R is visually perceived, the catheter assembly 1 is further advanced a distance in the tip direction. Specifically, the catheter 2 is advanced forward to a predetermined position inside the blood vessel by holding the tab 36 formed on the outer periphery surface of the catheter hub 3 with fingers.

If the blood vessel is secured by the catheter 2, the catheter 2 or the catheter hub 3 is fixed by one hand, while the needle hub 5 is grasped by the other hand to be pulled toward the base end direction. Then, the needle 4 is evulsed from the catheter 2 (see FIGS. 2 and 3). Accordingly, the catheter assembly 1 is in a disassembled state. At this time, since the opening and closing unit 71 of the valve element 7 is in a closed state in the indwelling catheter 11, the blood R inside the passage 31 is prevented from leaking out to the outside. In addition, since the above-mentioned sealing member 10 tightly contacting the valve element 7 is provided inside the catheter hub 3, it is possible to prevent the blood R from leaking out from the inside of the catheter hub 3 when the needle 4 is evulsed. Further, the evulsed puncturing needle 12 is no longer necessary, and is therefore discarded.

Next, the catheter hub 3 of the indwelling catheter 11 is fixed onto the skin using an adhesive tape or the like. Then, the connector 20 is connected to the catheter hub 3 (see FIG. 4). The operation member 8 is pressedly pushed by the connector 20 to be moved by connection in the tip direction such that the opening portion 85 of one side passes through the valve element 7. Accordingly, the passage 31 is in an open state.

Next, supply of the infusion solution Q is started. In this manner, the infusion solution Q, sequentially passing through the inside of the connector 20 and the inside of the operation member 8, flows out from the opening portion 85 of one side of the operation member 8, thereby filling the entire passage 31 with the infusion solution Q (priming) (see FIG. 4).

What is claimed is:

1. A catheter assembly comprising:
   a hollow catheter;
   a catheter hub fixed onto a base end portion of the catheter, the catheter hub having an internal passage communicating with an inside of the catheter;
   a needle disposed in the catheter;
   a needle hub fixed to a base end portion of the needle, the needle hub being connectable to a base end side of the catheter hub;
   a valve element positioned to block the internal passage of the catheter hub, the valve element including a tubular portion, and an opening and closing portion configured to be opened and closed, the opening and closing portion comprising at least one slit;

an operation member including a tubular body, the operation member being configured such that an opening portion of the operation member is insertable into the opening and closing portion to cause the base end side and a tip side of the catheter hub to communicate with each other;

a communication unit comprising at least one of a hole and a groove, the communication unit being disposed on at least one of (i) an inner periphery portion of the catheter hub where the valve element is positioned, and (ii) a peripheral edge portion of the valve element, wherein the communication unit is configured to allow the base end side and the tip side of the catheter hub to communicate with each other; and a sealing member including a tubular body, the sealing member being disposed at a base end side of the valve element and being configured to allow the passage of air and prohibit the passage of liquid, wherein the sealing member includes an extending portion that extends into the tubular portion of the valve element.

2. The catheter assembly according to claim 1, wherein the sealing member is a porous body.

3. The catheter assembly according to claim 1, wherein: the sealing member comprises:

a tubular molded article having a first end surface at which the tubular molded article contacts the valve element, and a second, opposing end surface, the tubular molded article including a hole portion passing through the sealing member from the first end surface to the second end surface, and a hydrophobic filter disposed in contact with the second end surface.

4. The catheter assembly according to claim 3, wherein the hole portion is coated with a water-swelling polymer.

5. The catheter assembly according to claim 1, wherein: the sealing member comprises:

a tubular molded article having a first end surface at which the tubular molded article contacts the valve element, and a second, opposing end surface, the tubular molded article including an outer peripheral groove portion formed on the outer periphery surface of the tubular molded body from the first end surface to the second end surface, and a hydrophobic filter disposed in contact with the second end surface.

6. The catheter assembly according to claim 5, wherein the outer peripheral groove portion is coated with a water-swelling polymer.

7. The catheter assembly according to claim 1, wherein an outer surface of the extending portion of the sealing member contacts an inner surface of the tubular portion of the valve element.

8. The catheter assembly according to claim 1, wherein the sealing member comprises a sintered body made of polyethylene.

9. The catheter assembly according to claim 1, wherein the sealing member is fixed to an inner peripheral surface of the catheter hub and is configured to inhibit displacement of the valve towards the base end side of the catheter hub.

* * * * *